(12) United States Patent
Arai (10) Patent No.: US 11,266,549 B2
(45) Date of Patent: Mar. 8, 2022

(54) TAPE-TYPE DISPOSABLE DIAPER

(71) Applicant: Daio Paper Corporation, Ehime (JP)

(72) Inventor: Hiroki Arai, Sakura (JP)

(73) Assignee: Daio Paper Corporation, Ehime (JP)

( * ) Notice: Subject to any disclaimer, the term of this patent is extended or adjusted under 35 U.S.C. 154(b) by 406 days.

(21) Appl. No.: 16/349,043

(22) PCT Filed: Nov. 22, 2017

(86) PCT No.: PCT/JP2017/041931
§ 371 (c)(1),
(2) Date: May 10, 2019

(87) PCT Pub. No.: WO2018/097160
PCT Pub. Date: May 31, 2018

(65) Prior Publication Data
US 2019/0282415 A1    Sep. 19, 2019

(30) Foreign Application Priority Data

Nov. 25, 2016   (JP) .............................. JP2016-229593

(51) Int. Cl.
*A61F 13/62* (2006.01)
*A61F 13/56* (2006.01)
(Continued)

(52) U.S. Cl.
CPC ............ *A61F 13/5644* (2013.01); *A61F 5/44* (2013.01); *A61F 13/56* (2013.01);
(Continued)

(58) Field of Classification Search
CPC .. A61F 13/56; A61F 13/5638; A61F 13/5644; A61F 13/62; A61F 13/622; A61F 13/627; A61F 2013/5688
See application file for complete search history.

(56) References Cited

U.S. PATENT DOCUMENTS 4,770,917 A * 9/1988 Tochacek ............... D04B 21/04
428/95
4,973,326 A * 11/1990 Wood .................... A61F 13/622
604/391

(Continued)

FOREIGN PATENT DOCUMENTS

EP    0 848 938    6/1998
JP    H11-42249    2/1999

(Continued)

OTHER PUBLICATIONS

International Search Report, PCT/JP2017/041931, dated Feb. 6, 2018.

*Primary Examiner* — Catharine L Anderson
(74) *Attorney, Agent, or Firm* — Andrus Intellectual Property Law, LLP (57) ABSTRACT

A nonwoven sheet is provided in a formation region of a target portion or a further wide region including the formation region of the target portion. The target portion is a composite of a nonwoven fabric as a base and loop pile fiber yarns which are woven and project from at least an external surface nonwoven fabric. The target portion is fixed to an outer nonwoven sheet forming the outside of a ventral part.

2 Claims, 13 Drawing Sheets

(51) Int. Cl.
*A61F 5/44* (2006.01)
*A61F 13/15* (2006.01)

(52) U.S. Cl.
CPC .......... *A61F 13/5638* (2013.01); *A61F 13/62* (2013.01); *A61F 13/622* (2013.01); *A61F 2013/1591* (2013.01); *A61F 2013/5688* (2013.01)

(56) References Cited

U.S. PATENT DOCUMENTS

| | | | |
|---|---|---|---|
| 5,476,702 A * | 12/1995 | Datta | A61F 13/627 428/157 |
| 5,542,942 A * | 8/1996 | Kline | A61F 13/627 604/385.29 |
| 5,707,707 A * | 1/1998 | Burnes | D04B 21/04 428/95 |
| 6,063,067 A | 5/2000 | Takizawa et al. | |
| 6,647,600 B1 * | 11/2003 | Jost | A61F 13/622 24/442 |
| 2006/0080810 A1 | 4/2006 | Horn et al. | |
| 2012/0089112 A1 * | 4/2012 | Horn | A61F 13/5638 604/391 |
| 2014/0039443 A1 | 2/2014 | Nagai et al. | |
| 2015/0238374 A1 | 8/2015 | Wildeman | |

FOREIGN PATENT DOCUMENTS

| | | |
|---|---|---|
| JP | H11-290103 | 10/1999 |
| JP | 2000-506427 | 5/2000 |
| JP | 2004-267257 | 9/2004 |
| JP | 2006-81720 | 3/2006 |
| JP | 2008-516742 | 5/2008 |
| JP | 2009-183797 | 8/2009 |
| JP | 2014-198177 | 1/2014 |
| JP | 2014-008276 | 10/2014 |
| JP | 5683982 | 1/2015 |
| JP | 2015-119782 | 7/2015 |

* cited by examiner

TAPE-TYPE DISPOSABLE DIAPER

CROSS-REFERENCE TO RELATED APPLICATIONS

This application is the U.S. national stage application of International Application PCT/JP2017/041931, filed Nov. 22, 2017, which international application was published on May 31, 2018, as International Publication WO 2018/097160 in the Japanese language. The International Application claims priority of Japanese Patent Application No. 2016-229593, filed Nov. 25, 2016. The international application and Japanese application are both incorporated herein by reference, in entirety.

TECHNICAL FIELD

The present invention relates to a tape-type disposable diaper.

BACKGROUND ART

A general tape-type disposable diaper has a ventral part, a dorsal part, a fastening tape, and a tape-shape target portion. The ventral part extends from the center in a front-back direction to a front side. The dorsal part extends on a back side. The fastening tape protrudes from both sides of the dorsal part. The tape-shape target portion is provided on an external surface of the ventral part. Upon wearing on the body, the fastening tape is extended from the left and right sides to the ventral side and detachably connected to an external surface of the target portion (refer to Patent Literatures 1 and 2, for example).

Such a tape-type disposable diaper is widely used for nursing (adult use) as well as being used for infants and children, and has an advantage that, by properly adjusting a connecting position of a fastening tape on the external surface of a target portion, the waist size can be adjusted.

When fastening tapes are roughly categorized, in addition to an adhesive tape type, there are also so-called mechanical fastener-type fastening tapes which are connected by hook and loop fasteners.

As a target portion in the latter mechanical fastener type, in general, fiber yarns are bonded on a plastic film as a base material in a linear shape while forming a loop.

A nonwoven sheet is generally used as an outer body in recent disposable diapers. As a result, the outer sheet is a nonwoven fabric, and in the target portion, a plastic film is used as a base material, and therefore an external surface of the product has different textures, and the presence of the target portion makes a consumer feel uncomfortable for the whole product.

CITATION LIST

Patent Literature

Patent Literature 1: JP 5683982 B2
Patent Literature 2: JP 2000-5-6427 A

SUMMARY OF INVENTION

Technical Problem

Accordingly, a main object of the present invention is to provide a tape-type disposable diaper having a target portion that provides a feeling of affinity with an outer nonwoven sheet.

Solution to Problem

The present invention that has solved the above problem will be described below.

A tape-type disposable diaper according to the present invention includes: a ventral part extending from the center in a front-back direction to a front side; a dorsal part extending to a back side; a fastening tape protruding from both sides of the dorsal part; and a target portion provided on an external surface of the ventral part, upon wearing on the body, the fastening tape being extended from left and right sides to a ventral side and detachably connected to the target portion, in which a nonwoven sheet is provided in a formation region of the target portion or a further wide region including the formation region of the target portion, the target portion is a composite of a nonwoven fabric as a base and loop pile fiber yarns which are woven in the nonwoven fabric and project from at least an external surface of the nonwoven fabric, and the target portion is fixed to an outer nonwoven sheet forming the outside of the ventral part.

In the present invention, there is used, as a target portion, a composite of a nonwoven fabric as a base and loop pile fiber yarns which are woven in the nonwoven fabric and project from at least an external surface of the nonwoven fabric. This target portion is fixed to an outer nonwoven sheet forming the outer side of the ventral part.

As a result, the outer nonwoven sheet forming the outer side of the ventral part and a composite obtained by weaving loop pile fiber yarns at least on the external surface with a nonwoven fabric as a base are common as a whole in the form of a nonwoven fabric. Therefore, it provides a feeling of affinity for purchasers and users of the products and provides the whole product with a high-class feeling.

Further, the target portion is not formed only with a pile knitted sheet, and the target portion is a composite of a nonwoven fabric as a base and loop pile fiber yarns which are woven in the nonwoven fabric and project from at least the external surface of the nonwoven fabric. Therefore, a sheet-like base made of the nonwoven fabric serves as a retaining anchor for pile fibers woven on a back surface side, and when the target portion is engaged with the fastening tape, coming out is prevented, and a high engaging force is obtained. Preventing the pile fibers from coming out is also a matter to be considered when a fastening position of the fastening tape is changed.

On the other hand, the composite may be fixed to the outer nonwoven sheet by a hot melt adhesive on the back surface side of the composite.

In this case, the composite may be fixed to the outer nonwoven sheet with a hot melt adhesive all over the back surface side.

The bonding strength between the composite and the outer nonwoven sheet is increased by fixing all over the back surface side.

On the other hand, the fixed region with the outer nonwoven sheet by the hot melt adhesive can also be a partial fixed region as follows, for example.

(1) The fixed region is provided along intersection rows of adjacent warps of the above-described warp group and is not provided between intersection rows.

(2) The amount of a hot melt adhesive in the region along intersection rows of adjacent warps of the above-described warp group is large, and the amount of a hot melt adhesive in the region between the intersection rows is small.

In the form of this partial fixed region, regions other than the fixed region or the region with a large coating amount by the hot melt adhesive have air permeability. Therefore, in combination with an outer nonwoven sheet having air permeability on the back surface side of the target portion, it is possible to obtain the product having air permeability as a whole.

In addition, since the intersection rows of adjacent warps of a warp group are fixed regions by a hot melt adhesive, the advantage of preventing pile fiber yarns in the intersection rows of the warps from coming off from the nonwoven sheet forming the base can be also obtained.

The outer nonwoven sheet may be disposed in a wide region extending from the ventral part including the formation region of the target portion to the dorsal part.

A condition in the present invention is that the target portion is a composite of a nonwoven fabric as a base and loop pile fiber yarns which are woven in the nonwoven fabric and project from at least the external surface of the nonwoven fabric. Thus, the whole of or most of the external surface of a disposable diaper can be a composite according to the present invention. In this case, a part of the ventral part is a target portion of a fastening tape.

In addition to the hot melt adhesive as a form for fixing the composite to the outer nonwoven sheet, the pile fiber yarns woven in a nonwoven fabric base and appearing on at least the back surface side of the nonwoven fabric base may be fixed to the outer nonwoven sheet in a heat sealed state.

Advantageous Effects of Invention

As described above, the present invention can provide a tape-type disposable diaper having a target portion that provides a feeling of affinity with an outer nonwoven sheet.

BRIEF DESCRIPTION OF DRAWINGS

FIG. 12(a) is a conceptual perspective view. FIG. 12(b) is a view from the X direction. FIG. 12(c) is a view from the Y direction.

DESCRIPTION OF EMBODIMENTS

Hereinafter, embodiments of the present invention will be described in detail with reference to the accompanying drawings.

First, an example of the structure of a disposable diaper will be described, and then an embodiment of the present invention will be described.

Note that a bonding means such as a hot melt adhesive and a bonded portion by a hot melt adhesive and the like are indicated by adding a dotted pattern in the drawing.

FIGS. 1 to 6 illustrate an example of a tape-type disposable diaper. This tape-type disposable diaper has a basic structure in which an absorber 3 is interposed between an inner surface of a liquid impervious sheet 1 and a liquid pervious top sheet 2.

(Absorber)

The absorber 3 is basically laminates of pulp fibers, assembly of filaments such as cellulose acetate, or nonwoven fabrics, and as necessary, super absorbent polymers can be mixed and fixed. Although the absorber 3 in the illustrated embodiment has a single layered structure, it may have a two-layered structure including a lower layer absorber and an upper layer absorber stacked thereon. Further, if necessary, the absorber 3 can be wrapped with crepe paper (not illustrated). Further, although the shape of the absorber 3 can be appropriately determined, a shape extending from the front side to the back side of the crotch portion such as a rectangular shape is preferable in addition to an hourglass shape as illustrated. It is desirable that pulp basis weight of the absorber 3 be about 100 to 500 g/m$^2$, and the thickness be about 1 to 15 mm. It is desirable that basis weight of the super absorbent polymer be about 0 to 300 g/m$^2$. When the content of the super absorbent polymer is too small, a sufficient absorbing ability cannot be imparted, and when the content is excessive, entanglement between the pulp fibers disappears, wrinkles, cracks and the like are likely to occur.

(Liquid Impervious Sheet)

The liquid impervious sheet 1 extends outwardly from the periphery of the absorber 3 and blocks movement of excretion absorbed by the absorber 3 to the back surface side. As the liquid impervious sheet 1, in addition to a plastic film such as a polyethylene film or the like, a sheet having moisture permeability without impairing imperviousness can be used from the viewpoint of prevention of stuffiness. A microporous sheet can be used for this waterproof/moisture pervious sheet, and the microporous sheet is obtained by stretching a sheet in one or two axial directions after forming the sheet by melt kneading an inorganic filler in polyolefinic resin such as polyethylene and polypropylene. The weight per unit area of the liquid impervious sheet 1 is preferably 13 to 40 g/m$^2$, and the thickness is preferably 0.01 to 0.1 mm.

To obtain the external surface of the diaper having a cloth-like appearance and texture, the entire back surface of the liquid impervious sheet 1 is covered with an outer nonwoven sheet 12, and the outer peripheral edges of both sheets 1 and 12 extend to the outer peripheral edges of the diaper. As the outer nonwoven sheet 12, various types of nonwoven fabrics can be used, but spunbonded nonwoven fabrics are preferable.

(Top Sheet)

As the top sheet 2, a porous or nonporous nonwoven fabric, a porous plastic sheet or the like is used. As the material fibers constituting the nonwoven fabric, not only synthetic fibers of polyolefin type such as polyethylene or polypropylene, polyester type, amide type and the like, regenerated fiber such as rayon and cupra, natural fiber such as cotton can be used. As the processing method of a nonwoven fabric, a known method such as a spun lace method, a spunbond method, an SMS method, a thermal bond method, a melt blown method, a needle punch method, an air-through method, and a point bond method can be used. The fiber basis weight of the nonwoven fabric used for the liquid pervious top sheet 2 is preferably 15 to 30 g/m², and the thickness is preferably 0.05 to 1 mm.

The top sheet 2 extends outwardly from the periphery of the absorber 3, and a portion extending outward from the side edge of the absorber 3 is fixed to the liquid impervious sheet 1 with a hot melt adhesive or the like. Note that the dotted pattern in the drawing represents a fixed portion.

(Three-Dimensional Gathers Around Legs)

Figure 3:
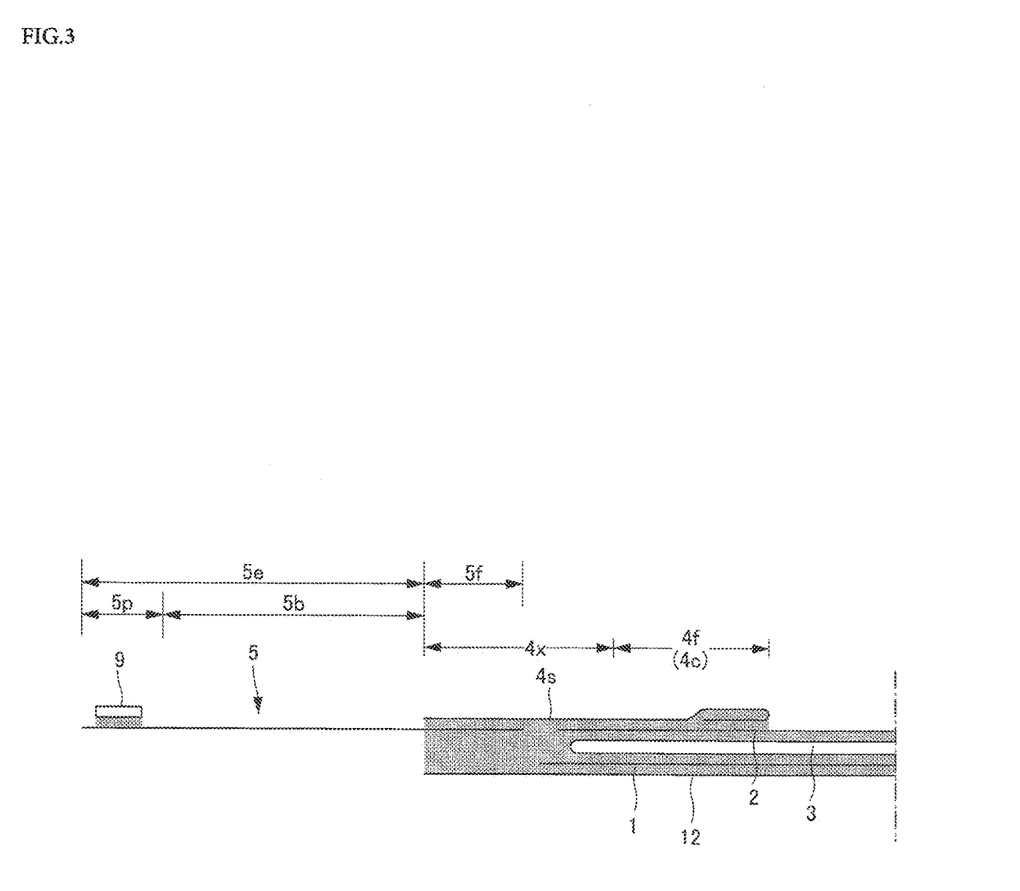
FIG. 3 is a sectional view taken along line iii-iii in FIG. 1.
Figure 4:
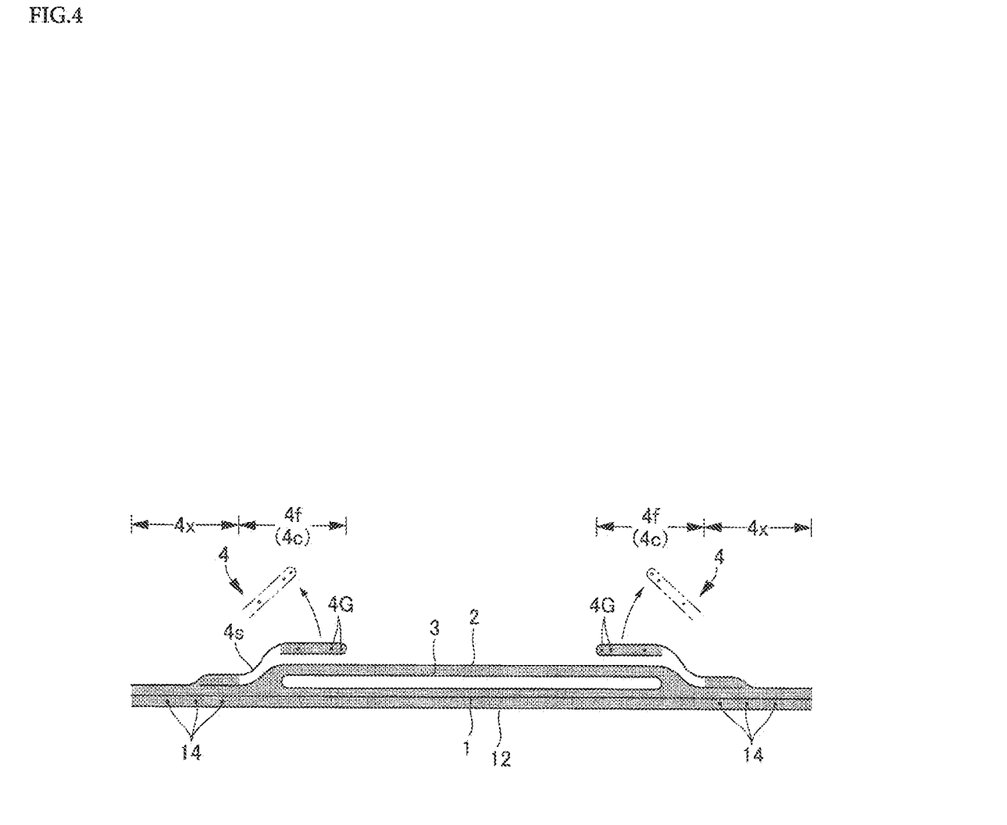
FIG. 4 is a sectional view taken along line iv-iv in FIG. 1.
Figure 5:
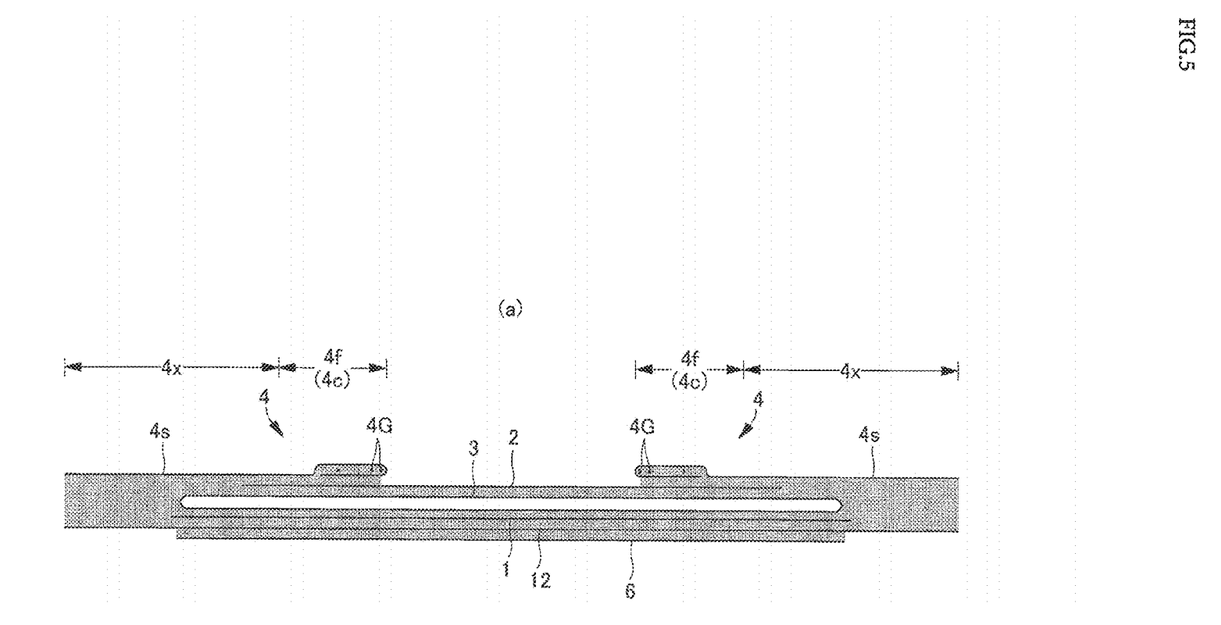
FIG. 5 is a sectional view taken along line ii-ii in FIG. 1.

As also illustrated in FIGS. 3 to 5, on both sides of the inner surface of the article (in the illustrated embodiment, the surface of the liquid impervious sheet 1 extending from the side edge surface of the top sheet 2 to the side thereof), a root-side portion 4x on the outer side in the width direction of around-leg three-dimensional gather sheets 4s forming around-leg three-dimensional gathers 4 is adhered all over in the front-back direction. For the around-leg three-dimensional gather sheets 4s, in addition to various nonwoven fabrics (spunbonded nonwoven fabrics are preferable), plastic films similar to those used for liquid impervious sheets, or laminated sheets thereof can be used, but from the viewpoint of feeling to the skin, a nonwoven fabric subjected to water repellent treatment is preferable. A protruding portion 4c on the center side in the width direction of the around-leg three-dimensional gather sheets 4s is fixed to the inner surface of the article (the surface of the top sheet 2 in the illustrated embodiment) in a fallen state at both ends in the front-back direction by a means such as a hot melt adhesive and regarded as a fallen part. The intermediate portion therebetween is an unfixed free part, and an elongated elastically stretchable member 4G is fixed with a hot melt adhesive or the like in a state of being elongated along the front-back direction at a tip portion or the like (an end portion on the center side in the width direction in a spread state) of this free part. In the illustrated example, a plurality of elongated elastically stretchable members 4G are provided with predetermined intervals, but one elongated elastic member 4G may be provided. As the elongated elastically stretchable member 4G (the same applies to other elongated elastically stretchable member), the materials which are usually used, such as natural rubber or synthetic rubber which are formed in a thread-like shape, a stripe-like shape, a band-like shape, and the like, specifically such as styrene rubber, olefin rubber, urethane rubber, ester rubber, polyurethane, polyethylene, polystyrene, styrene butadiene, silicon, polyester, and the like can be used. As a result of the contraction force of the elongated elastically stretchable member 4G acting on this free part, as illustrated in FIG. 4, the free part forms around-leg three-dimensional gathers standing with respect to the inner surface of the article (the surface of the top sheet 2 in the illustrated embodiment). A base end 4b of the standing part is positioned at the boundary between a fixed portion 4x and a portion 4c on the outside and inside, respectively, in the width direction in the around-leg three-dimensional gathers 4.

At both ends in the front-back direction of a disposable diaper, each of the liquid impervious sheet 1, an outer nonwoven sheet 12, the liquid pervious top sheet 2, and the around-leg three-dimensional gather sheets 4s extend to the front and back sides from the front and back ends of the absorber 3, and an end flap portion EF in which the absorber 3 is not provided is formed. On the other hand, on the lateral sides of the disposable diaper, each of the liquid impervious sheet 1, the outer nonwoven sheet 12, the liquid pervious top sheet 2, the around-leg three-dimensional gather sheets 4s extend to the lateral side with from the side edges of the absorber 3, and the side flap portion SF in which the absorber 3 is not provided is formed. The portion positioned at the waist side portion of the ventral part F and the waist side portion of the dorsal part B of the side flap portion SF extends longer to the lateral sides than the intermediate portion therebetween. These portions form a lower torso of the diaper, the intermediate portion forms the leg-surrounding portions LH, and both side edges form edges Le of the leg openings.

(Flat Gather)

At the intermediate portion in the front-back direction of the side flap portion SF, the elongated elastic member 7 is fixed between the liquid impervious sheet 1 and the outer nonwoven sheet 12 in a state of being stretched in the front-back direction by a hot melt adhesive or the like, and by this contraction of the elongated elastic member 7, a so-called flat gather is formed in the side flap portion SF. With this flat gather, the side portion of the diaper elastically expands and contracts to fit around the legs.

Although the number of the elongated elastic members 7 on each of the left and right sides can be determined as appropriate, about 1 to 10, more preferably about 3 to 8, is appropriate. In the case of plural, the interval is preferably about 2 to 15 mm, particularly about 6 to 10 mm. In addition, as each elongated elastic member 7, the materials which are usually used, such as polystyrene rubber, polyolefin rubber, polyurethane rubber, polyester rubber, polyurethane, polyethylene, polystyrene, polystyrene butadiene, silicone, polyester, and the like which are formed in a thread-like shape, a stripe-like shape, a band-like shape, and the like can be used. The fineness is preferably about 500 to 1500 dtex, and in the case of natural rubber, the fineness is preferably about 0.1 to 3 mm, more preferably about 0.5 to 3 mm. In addition, the stretch rate at the time of fixing each elongated elastic member 7 is preferably about 150 to 250%.

(Fastening Tape)

On the side flap portion SF of the dorsal part B, fastening tapes 5 projecting from the side edges thereof are attached, and the target portion 6 is adhered to a surface of the lower torso of the ventral part F along the width direction. Upon wearing on the body, with a diaper 100 applied to the body, the fastening tapes 5 on both sides are turned from the left and right sides to the ventral side and connected to the target portion 6.

Figure 1:
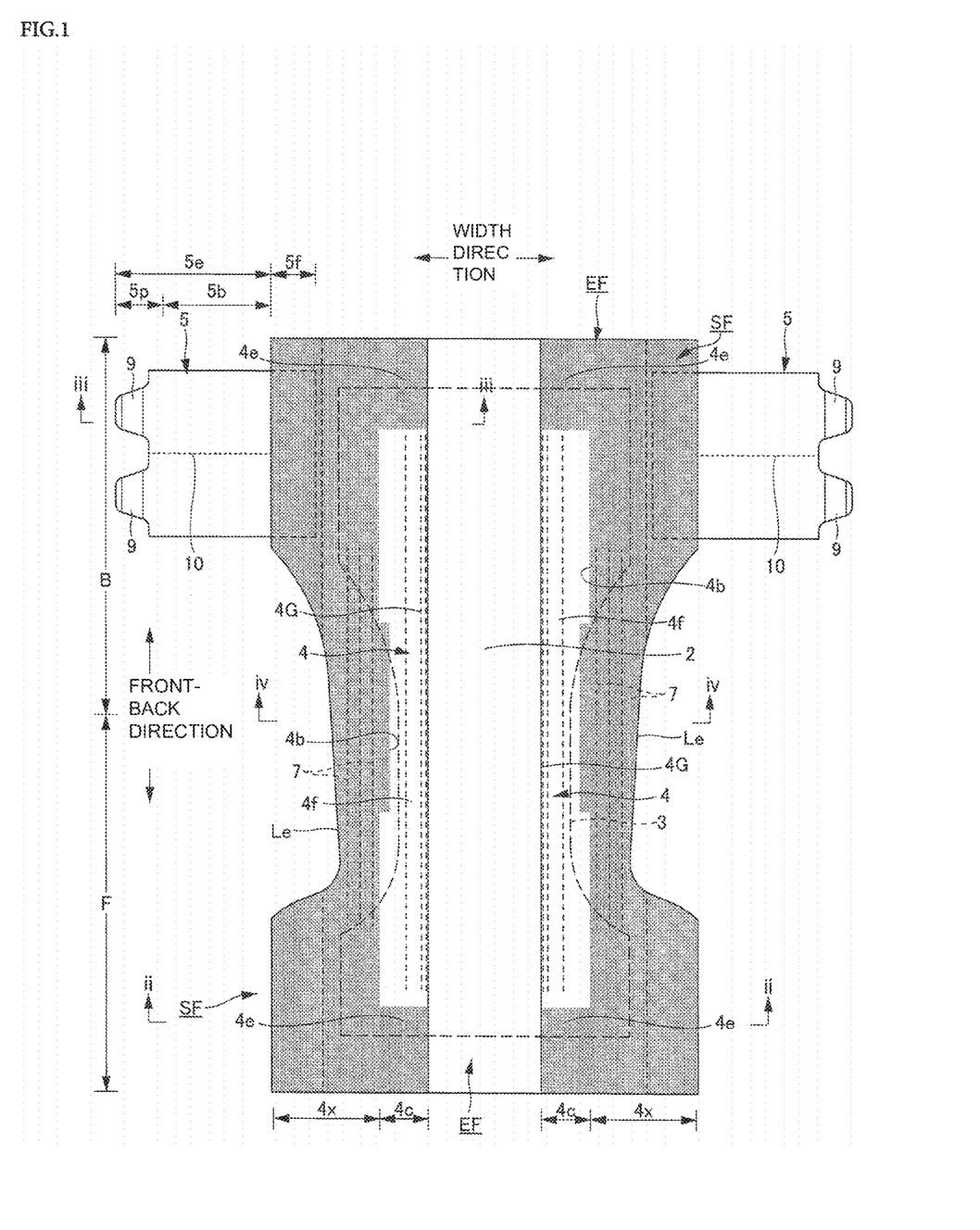
FIG. 1 is a plan view illustrating the inner surface side of a tape-type disposable diaper in a spread state.
Figure 2:
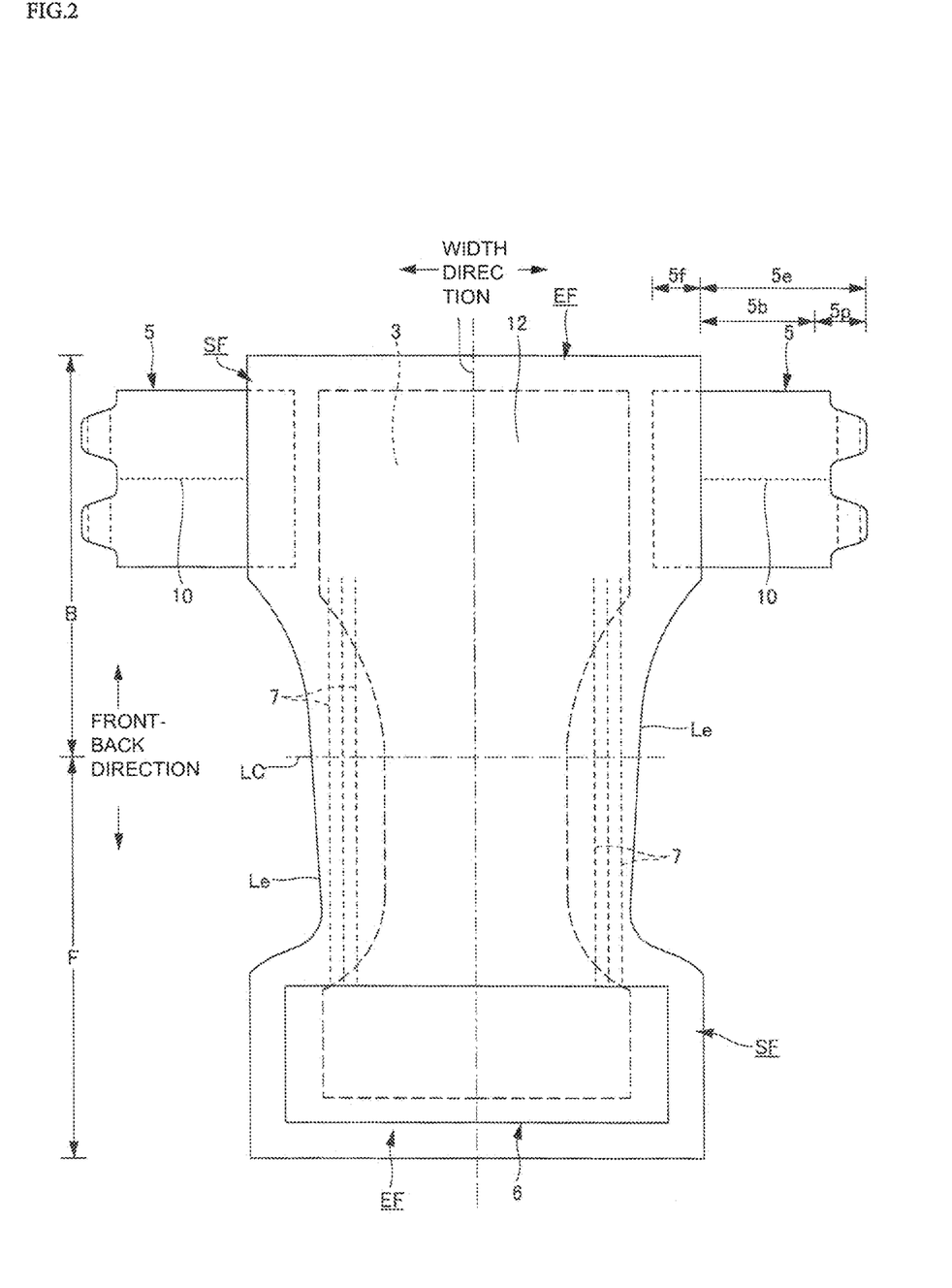
FIG. 2 is a plan view illustrating the external surface side of a tape-type disposable diaper in a spread state.

As illustrated in FIGS. 2 and 3, the fastening tapes 5 have a fixed part 5f and a projecting portion 5e. The fixed part 5f is fixed between the sheets at the waist side side flap portion SF of the dorsal part B by a means such as a hot melt adhesive or the like. The projecting portion 5e is projecting outward in the width direction from between the sheets at the side edges of the side flap portion SF. The projecting portion 5e includes a tip portion 5p and a main unit section 5b on the base end side of the tip portion 5p. On the internal surface side (the top sheet 2 side) of the tip portion 5p of the fastening tape 5, as a fixed part for coupling with the target portion 6, hook members (hook member of mechanical fasteners (hook and loop fastener)) 9, 9 each having a large number of hook-shape projections are attached to the surfaces thereof.

Figure 6:
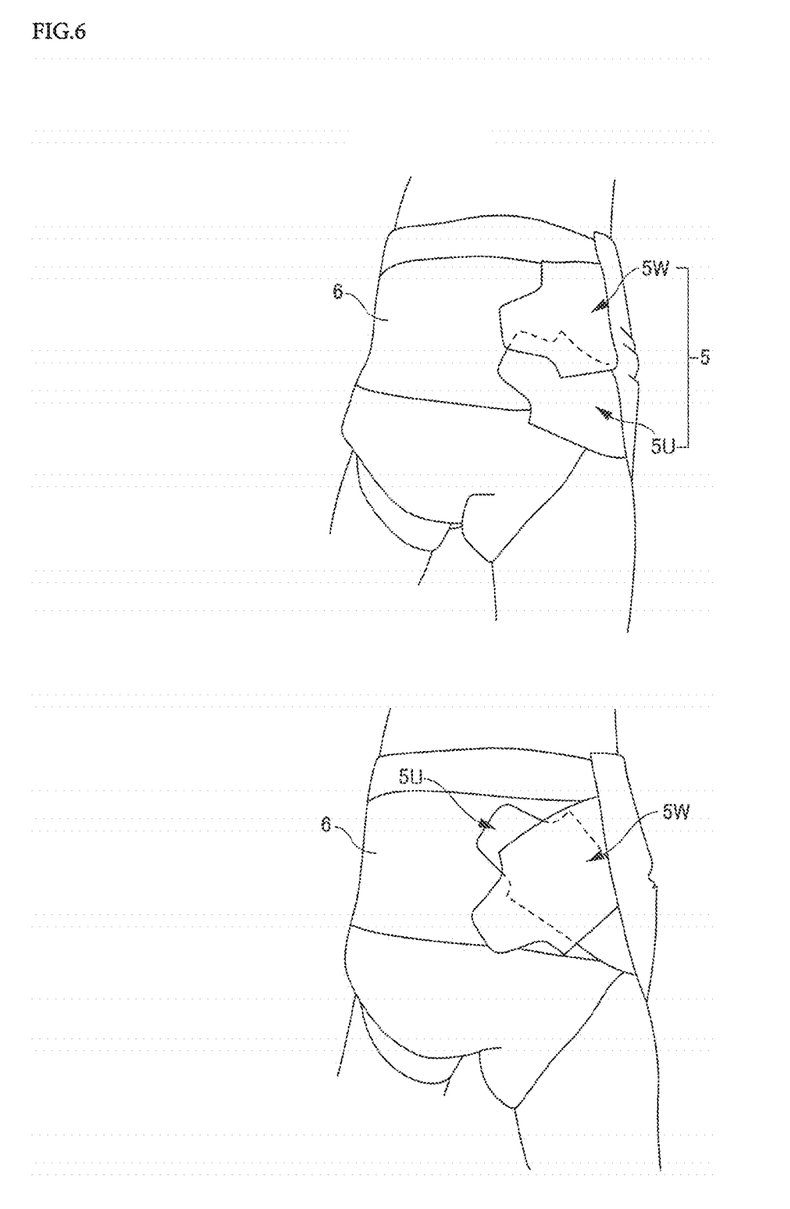
FIG. 6 is a perspective view schematically illustrating a wearing state of a tape-type disposable diaper.
Figure 7:
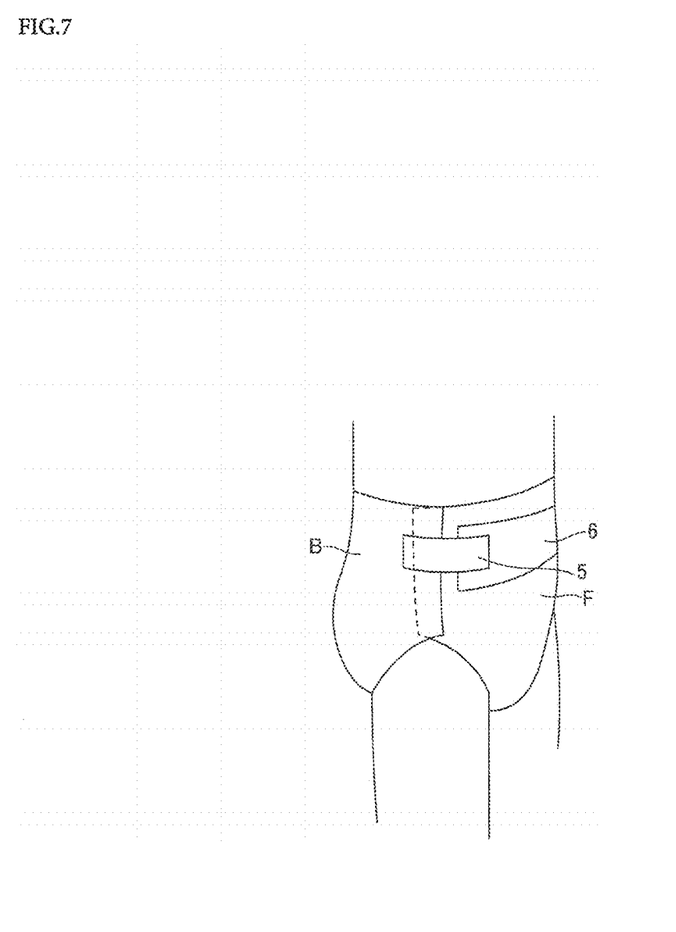
FIG. 7 is a perspective view schematically illustrating a wearing state of a tape-type disposable diaper.

Further, as illustrated in FIG. 2, perforations 10 along the width direction are provided on the fastening tape 5 from the outer side edge in the width direction at the intermediate portion in the up-down direction to the inside of the main unit section 5b. By splitting it along the perforations 10, as illustrated in FIG. 6, the fastening tape 5 can be separated into an upper step portion 5W and a lower step portion 5U each having a fixed part, a main unit section, a tip portion, and a fixed part. Instead of providing the perforation 10, it may be separated beforehand by cutting or the like. As illustrated in FIG. 6, in a state where the upper step portion 5W and the lower step portion 5U cross each other, the fastening tape 5 can be detachably connected to the target portion 6 of the ventral part F. It is obvious that it is not limited to such upper and lower division type, as illustrated in FIG. 7, the fastening tape 5 can be applied to other well-known fastening tapes such as a type not divided into two.

(Target Portion)

The target portion 6 is for reliable and easy attachment and detachment of the fastening tape 5. In the case where the fixed part of the fastening tape 5 is formed by the hook member 9, a sheet material having a surface on which the hook-shape projections are detachably engaged, for example, a loop member of a mechanical fastener (hook and loop fastener) or a nonwoven fabric can be used. When an adhesive layer is used instead of the hook member 9, a resin sheet that can sufficiently exert its adhesiveness can be used.

The shape of the target portion 6 is not particularly limited as long as it extends to both sides in the width direction. In addition to the rectangular shape, which is elongated in the width direction and is widely used at present as in the illustrated embodiment, it may be a substantially rectangular shape obtained by cutting each side into a wavy shape or the like, or elliptical shape elongated in the width direction. In the case of an embodiment having a plurality of the fastening tapes 5 in the longitudinal direction and an embodiment having a plurality of projecting portions independently connected to the target portion 6 in the vertical direction, for example, it is also possible to provide a plurality of the target portions 6 in the vertical direction.

The size of the target portion 6 is not particularly limited, but it is desirable that the size of the central portion 6C in the width direction fixed to the external surface of the ventral part F is about 30 to 70% of a product width X (a portion excluding the target portion 6 and the fastening tape 5, the same applies to below). In addition, it is desirable that the size of a side portion 6S be set to about 10 to 30% of the product width X in a spread state.

The size of the target portion 6 is not particularly limited, but it is desirable that, in a state in which the ventral side portion FS is expanded, the size be about 60 to 90% of a product width X2 in a spread state. In addition, it is desirable that the product width X1 of the ventral side portion FS in a folded state be about 10 to 40% of the product width X2 in a spread state.

<Composite and Fixed Form Thereof>

As the target portion 6 in the above example, in the present invention, it is particularly desirable to use, for example, the composite illustrated in FIGS. 8 to 13.

As illustrated in FIG. 2, the target portion 6 in the embodiment is disposed in the formation region of the target portion 6 or a further wide region including the formation region of this target portion, for example, a further wide region from the ventral part to the dorsal part.

The target portion 6 is composed of a composite 62 of a nonwoven fabric 60 and a pile of pile fiber yarns 61. Specifically, pile fiber yarns are knitted with the nonwoven fabric 60 as a base, and loop pile fiber yarns 61a are formed at least on the external surface.

Figure 8:
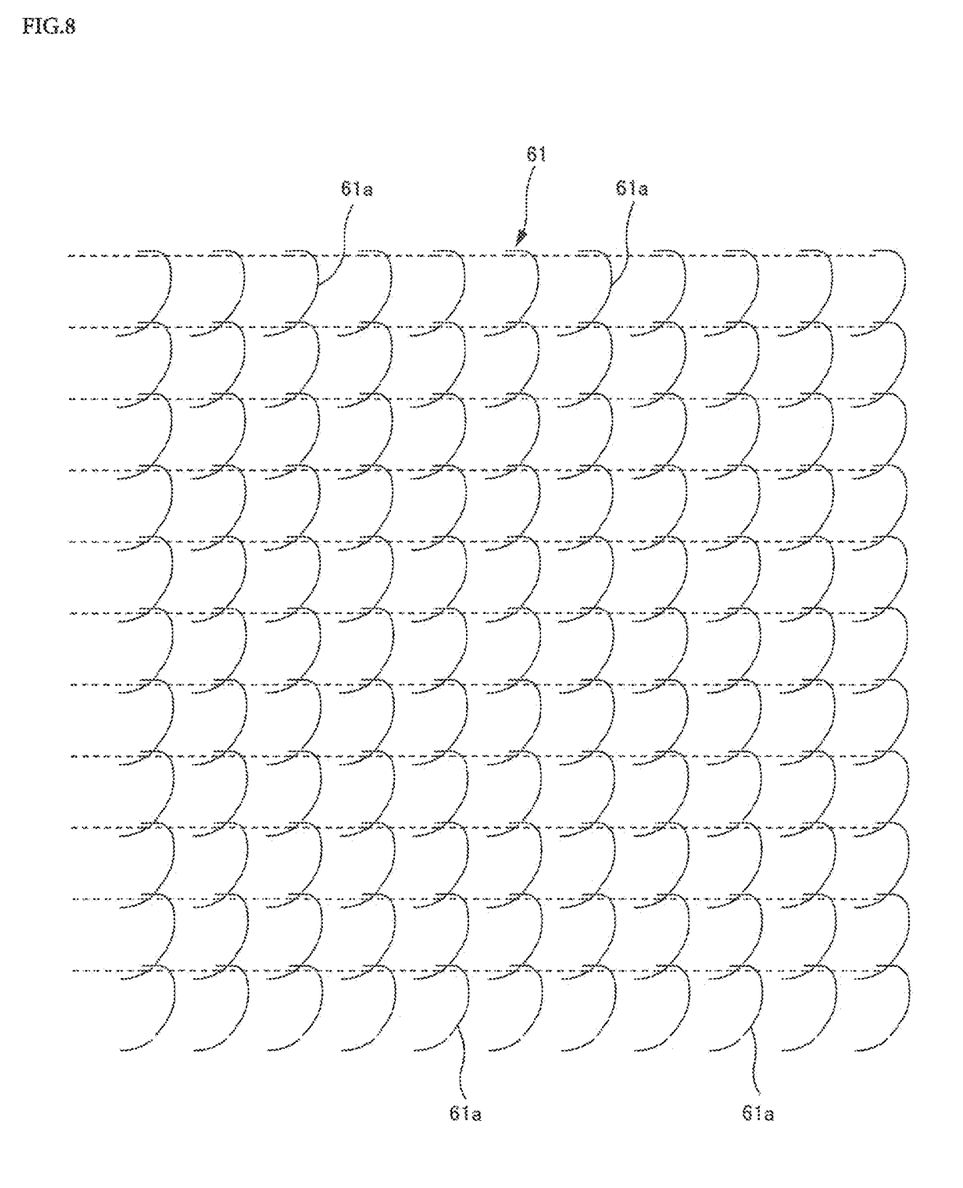
FIG. 8 is a conceptual view for explaining an external surface side of a composite.
Figure 9:
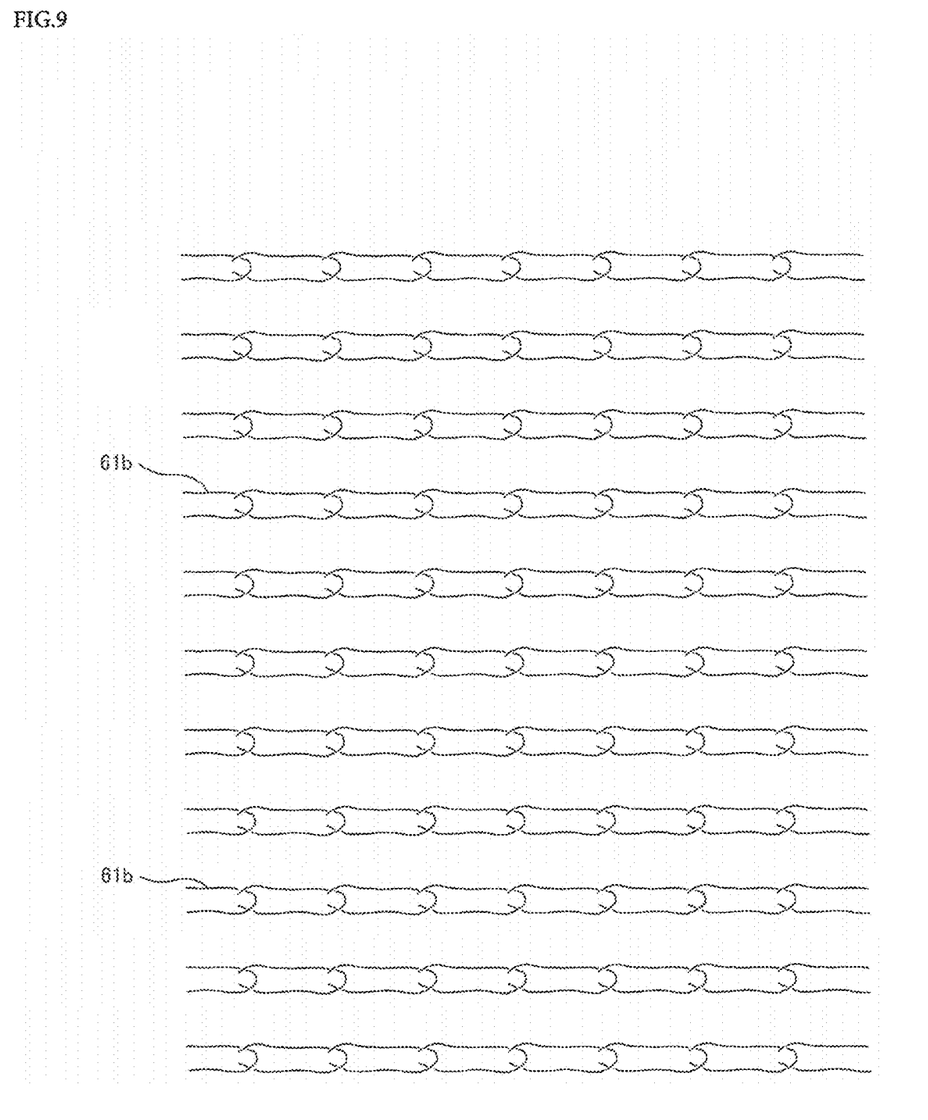
FIG. 9 is a conceptual view for explaining an external surface side of a composite.

The pile is formed as a knitted fabric by knitting the pile fiber yarns 61 continuously, for example, in the radial direction (lateral direction: lateral direction in FIGS. 8 and 9).

Figure 12:
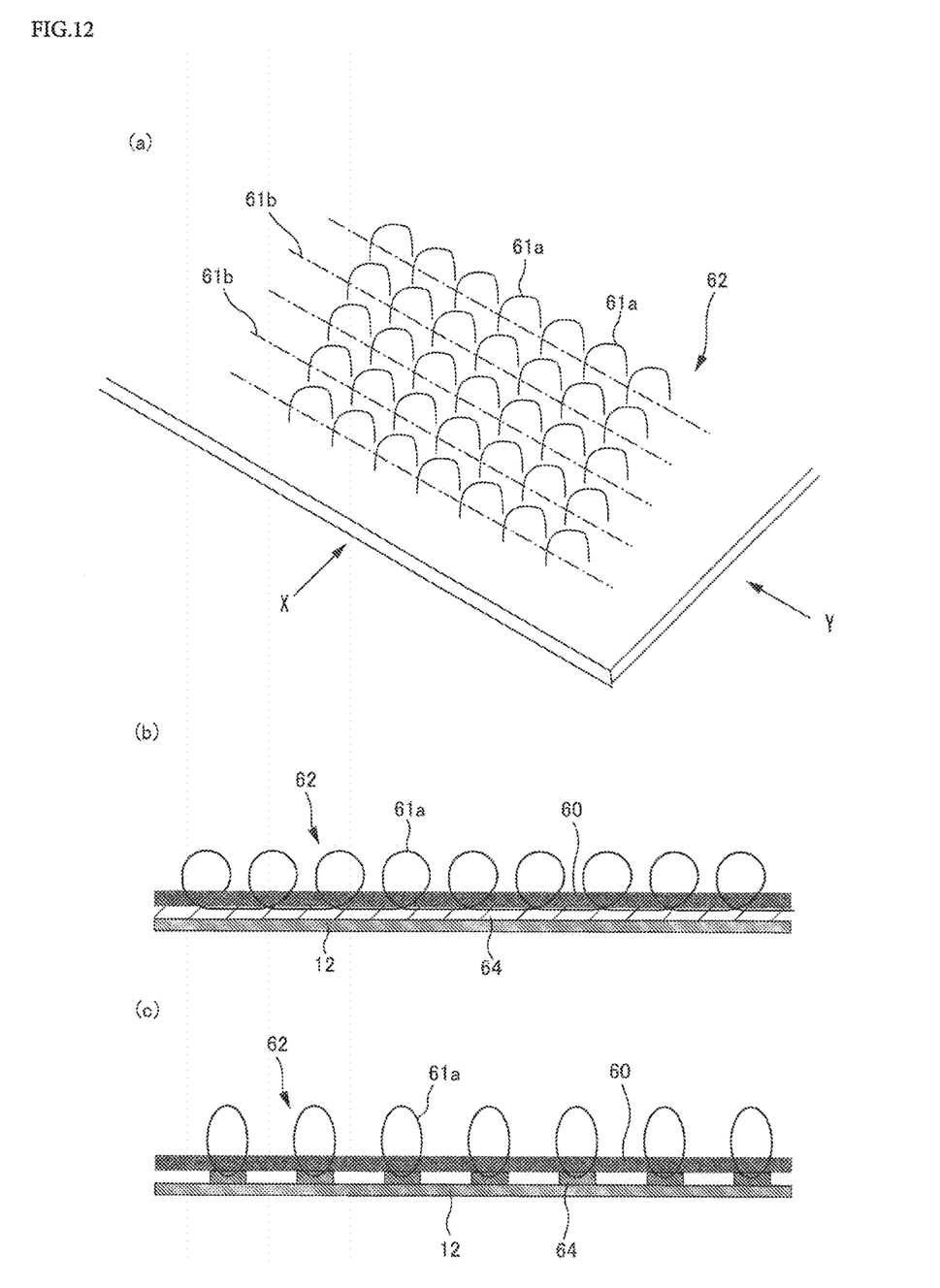
FIG. 12 is a view for explaining a composite bonding example by a hot melt adhesive.

As illustrated in FIGS. 8 and 12, the loop pile fiber yarns 61a are formed to protrude at intervals in the weft directions on the external surface of the nonwoven fabric 60, that is, on the external surface side of the disposable diaper.

On the other hand, on the back surface side (wearer side) of the nonwoven fabric 60, the pile fiber yarns 61 are combined with each other to form intersection rows 61b of the pile fiber warps.

As described above, the composite 62 is fixed to the outer nonwoven sheet 12 forming the outside of the ventral part by a hot melt adhesive, heat sealing or the like as the target portion 6.

In this case, the composite 62 may be fixed to the outer nonwoven sheet 12 with a hot melt adhesive 64 all over the back surface side.

The bonding strength between the composite 62 and the outer nonwoven sheet 12 is increased by fixing all over the back surface side.

On the other hand, the fixed region with the outer nonwoven sheet 12 by the hot melt adhesive 64 can also be a partial fixed region as follows, for example.

(1) As illustrated in FIG. 12, a form in which a fixed region is not provided along intersection rows 61b of adjacent warps of a warp group and between the intersection rows 61b and 61b.

(2) A form in which the amount of a hot melt adhesive in the region along intersection rows 61b of adjacent warps of a warp group is large, and the amount of a hot melt adhesive in the region between the intersection rows 61b and 61b is small.

In the form of this partial fixed region, regions other than the fixed region or the region with a large coating amount by the hot melt adhesive 64 have air permeability. Therefore, in combination with the outer nonwoven sheet 12 having air permeability on the back surface side of the target portion, it is possible to obtain a product having air permeability as a whole.

In addition, since the intersection rows 61b of adjacent warps of a warp group are fixed regions by a hot melt adhesive, the advantage of preventing pile fiber yarns positioned in the intersection rows 61b of the warps from coming off from the nonwoven fabric 60 constituting the base can be also obtained.

Figure 13:
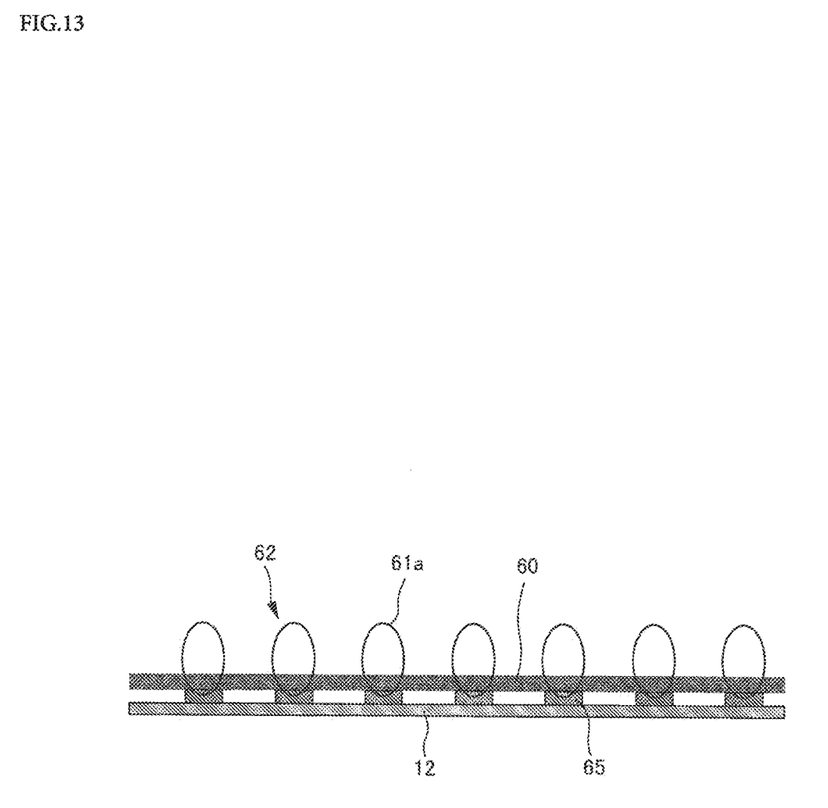
FIG. 13 is a cross-sectional view of a composite example having a heat sealed portion.

In addition to the hot melt adhesive as a form for fixing the composite 62 to the outer nonwoven sheet 12, as illustrated in FIG. 13, the pile fiber yarns 61 (the intersection rows 61b of warps in the embodiment) woven and appearing on at least the back surface side of the nonwoven fabric 60 substrate may be fixed to the outer nonwoven sheet 12 in a heat sealed state. Reference sign 65 denotes a heat sealed portion.

In this case, if the heat-sealed portion is entirely provided, the rigidity becomes high. Therefore, it is desirable to have a partial fixing (bonding) form in which only a portion along the intersection rows 61b of warps is heat sealed.

The material of the nonwoven fabric forming the composite 62 is not necessarily limited, but the material which has been already described can be used. That is, as the material fibers constituting the nonwoven fabric, not only synthetic fibers of polyolefin type, polyester type, polyamide type and the like such as polyethylene or polypropylene, regenerated fiber such as rayon and cupra, natural fiber such as cotton can be used. As the processing method of a nonwoven fabric, a known method such as a spun lace method, a spunbond method, an SMS method, a thermal bond method, a melt blown method, a needle punch method, an air-through method, and a point bond method can be used.

The fiber basis weight of the nonwoven fabric is preferably 15 to 30 $g/m^2$, and the thickness is preferably 0.05 to 1 mm.

Although it is preferable that one nonwoven fabric is used as a base, stacked nonwoven fabrics can be used if necessary.

Examples of knitted pile fiber yarns include weft pile weave and warp pile weave, and in addition, include leno weave fabric such as plain gauze and gauze texture, and figured fabric such as dobby and jacquard weaves.

In the present invention described according to the above-described embodiment, as the target portion 6, the composite 62 is used in which the nonwoven fabric 60 is used as a base and loop pile fiber yarns are woven in the nonwoven fabric and project from at least the external surface thereof. This target portion 6 is fixed to the outer nonwoven sheet 12 forming the outside of the ventral part.

As a result, the outer nonwoven sheet 12 forming the outside of the ventral part and the composite 62 of a nonwoven fabric as a base and the loop pile fiber yarns 61a which are woven in the nonwoven fabric and project from at least the external surface of the nonwoven fabric are common as a whole in the form of a nonwoven fabric. Therefore, it provides a feeling of affinity for purchasers and users of the products and provides the whole product with a high-class feeling.

Further, the target portion 6 is not formed only with the pile knitted sheet, and the target portion 6 is the composite 62 of the nonwoven fabric 60 as a base and the loop pile fiber yarns which are woven in the nonwoven fabric and project from at least on the external surface of the nonwoven fabric. Therefore, the sheet-like base made of the nonwoven fabric 60 serves as a retaining anchor for the pile fibers woven on the back surface side, and when it is engaged with the fastening tape, coming out is prevented, and a high engaging force is obtained.

Figure 10:
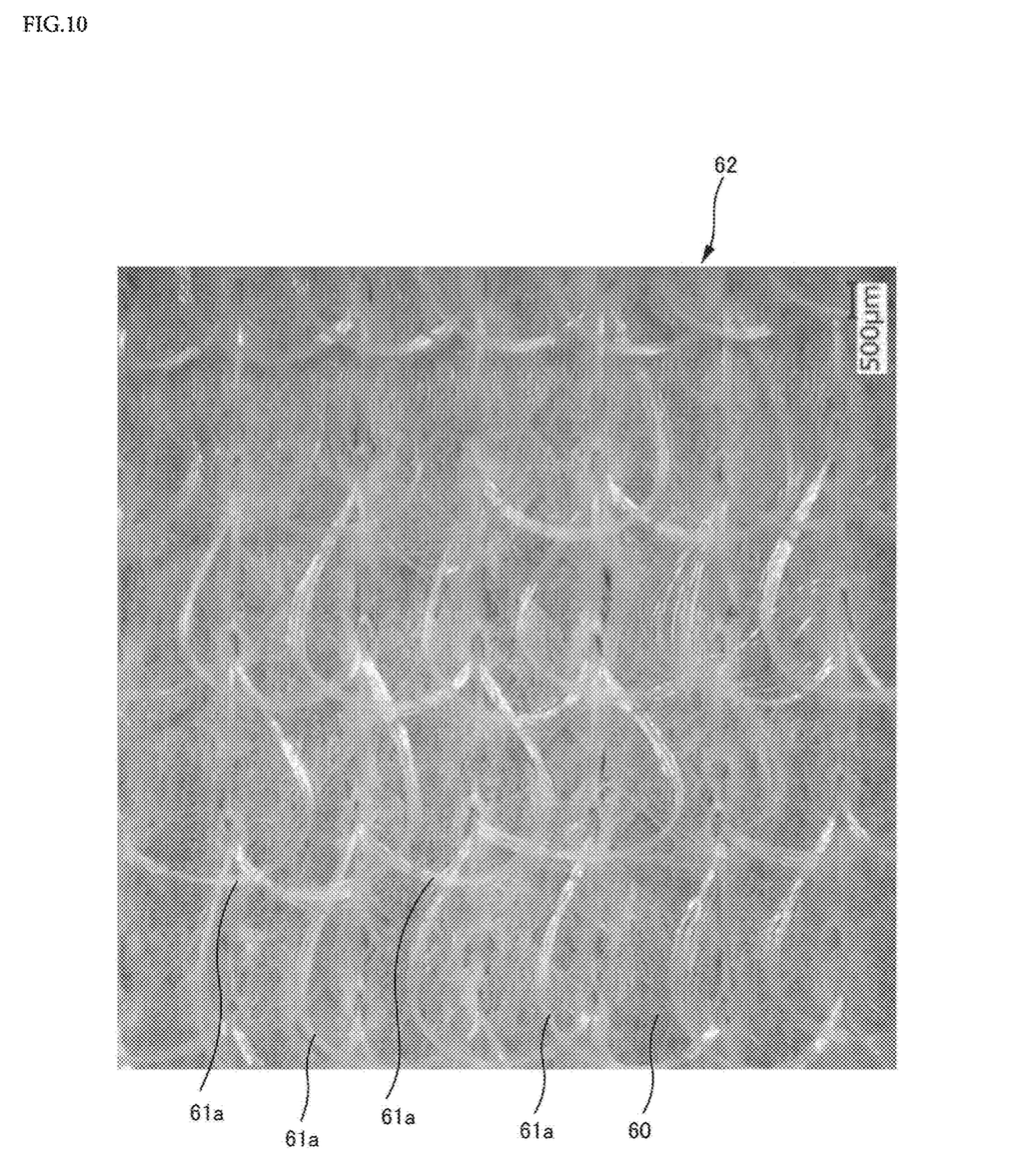
FIG. 10 is a photograph of an external surface side of a composite example.
Figure 11:
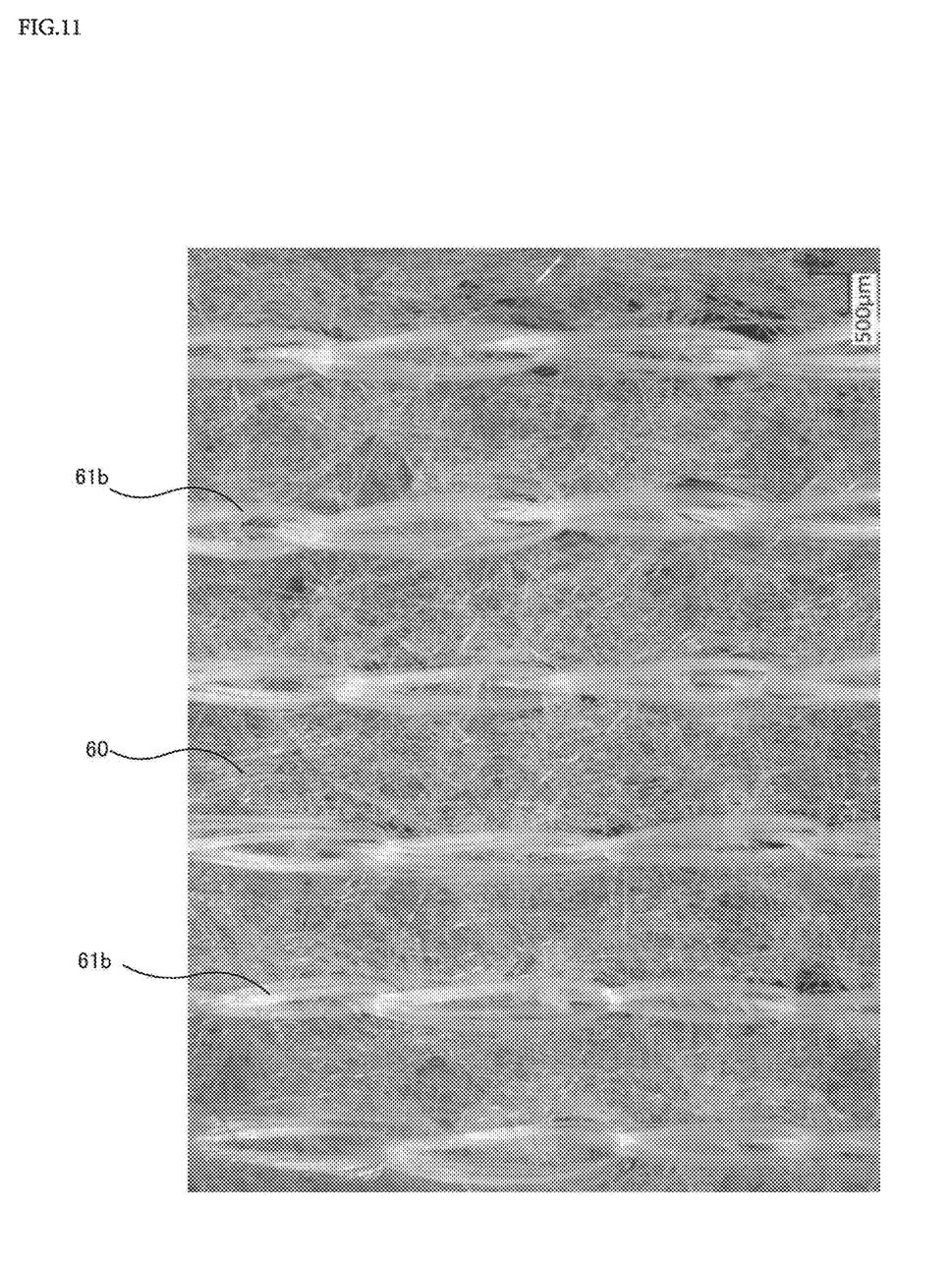
FIG. 11 is a photograph of a back surface side of a composite example.

Now that, supplementally referring to the drawings, FIG. 8 illustrates rows of the loop pile fiber yarns 61a on the external surface of the composite 62, and the braid on the back surface is not illustrated. FIG. 10 indicates a photograph taken of an actual example. FIG. 9 illustrates the intersection rows 61a of the warps on the back surface of the composite 62. The loop pile fiber yarns 61a on the external surface is not illustrated. FIG. 11 indicates a photograph taken of an actual example.

INDUSTRIAL APPLICABILITY

The present invention is applicable to a tape-type disposable diaper as in the above embodiments.

REFERENCE SIGNS LIST 1 liquid impervious sheet
2 top sheet
3 absorber
4 around-leg three-dimensional gathers
4f free part
4e fallen part
5 fastening tape
6 target portion
9 hook material
10 perforation
12 outer nonwoven sheet
F ventral part
B dorsal part
60 nonwoven fabric
61 pile fiber yarn
61a loop pile fiber yarn
61b intersection row
62 composite

The invention claimed is:

1. A tape-type disposable diaper, comprising:
a ventral part extending from the center in a front-back direction to a front side; a dorsal part extending to a back side; a fastening tape protruding from both sides of the dorsal part; and a target portion provided on an external surface of the ventral part,
wherein upon wearing on the body, the fastening tape extends from left and right sides to a ventral side and is detachably connected to the target portion,
wherein an outer nonwoven sheet forming an outside of the ventral part is provided in a formation region of the target portion or a further wide region including the formation region of the target portion,
wherein the target portion is a composite having a nonwoven fabric as a base and loop pile fiber yarns which are formed of pile fiber yarns knitted into the nonwoven fabric as the base on at least an external surface thereof, and
wherein on a back surface side of the nonwoven fabric as the base, the pile fiber yarns are combined with each other to form intersection rows of pile fiber warps,
wherein the composite is fixed to the outer nonwoven sheet by a hot melt adhesive on the back surface side of the nonwoven fabric as the base, and
wherein a fixed region with the outer nonwoven sheet by the hot melt adhesive is provided along intersection rows of adjacent warps of a warp group of the pile fiber warps and is not provided between the intersection rows.

2. The tape-type disposable diaper according to claim 1, wherein the outer nonwoven sheet is disposed in the further wide region including the formation region of the target portion from the ventral part to the dorsal part.

* * * * *